United States Patent [19]

Freed

[11] Patent Number: 5,398,679

[45] Date of Patent: Mar. 21, 1995

[54] HINGED ENDOTRACHEAL TUBE HOLDER HAVING BOTH A SAFETY CLAMP AND A SECURING CLAMP

[76] Inventor: M. Simon Freed, 289 Walpole St., Norwood, Mass. 02062

[21] Appl. No.: 121,154

[22] Filed: Sep. 13, 1993

[51] Int. Cl.$^6$ .................. A61M 16/00; A62B 9/06
[52] U.S. Cl. .................. 128/207.17; 128/912; 128/DIG. 26
[58] Field of Search .................. 128/200.26, 207.17, 128/912, DIG. 26, 207.14

[56] References Cited

U.S. PATENT DOCUMENTS

| | | | |
|---|---|---|---|
| 3,993,081 | 11/1976 | Cussell | 128/DIG. 26 |
| 4,209,015 | 6/1980 | Wicks | 128/DIG. 26 |
| 4,249,529 | 2/1981 | Nestor et al. | 128/DIG. 26 |
| 4,270,529 | 6/1981 | Muto . | |
| 4,326,515 | 4/1982 | Shaffer et al. . | |
| 4,329,984 | 5/1982 | Kervin . | |
| 4,351,331 | 9/1982 | Gereg . | |
| 4,449,527 | 5/1984 | Hinton . | |
| 4,530,354 | 7/1985 | Froilan | 128/207.17 |
| 4,548,200 | 10/1985 | Wapner . | |
| 4,683,882 | 8/1987 | Laird | 128/207.17 |
| 4,774,944 | 10/1988 | Mischinski | 128/207.17 |
| 4,832,019 | 5/1989 | Weinstein et al. . | |
| 4,896,667 | 1/1990 | Magnuson et al. . | |
| 5,026,352 | 6/1991 | Anderson | 128/207.17 |
| 5,069,206 | 12/1991 | Crosbie | 128/207.17 |
| 5,233,979 | 8/1993 | Strickland | 128/207.17 |

*Primary Examiner*—Kimberly L. Asher
*Attorney, Agent, or Firm*—Fish & Richardson

[57] ABSTRACT

A holder for retaining an endotracheal tube in a patient's mouth has upper and lower portions, each including a semi-cylindrical member with wings extending radially on opposite sides. The upper and lower portions are joined by a flexible hinge between a first wing of the upper portion and an opposed first wing of the lower portion. When the hinge is closed, a region of each upper wing is adjacent to a region of a corresponding opposed lower wing, and the semi-cylindrical members form a sleeve defining a lumen sized to receive the endotracheal tube. A safety clamp limits the extent to which the upper and lower portions can pivot apart about the hinge to a predetermined maximum angle, whereby the position of the endotracheal tube can be adjusted axially, but radial displacement of the tube from the holder is restricted. A securing clamp relatively more spaced from the hinge moves between a first position, in which the upper and lower portions are allowed to pivot to the extent allowed by the safety clamp, to allow for axial adjustment of the endotracheal tube while limiting radial movement, and a second position in which the sleeve engages the tube to also limit axial movement of the tube relative to the holder. In use, the endotracheal tube is inserted through a patient's mouth into the tracheal lumen, the safety clamp of the tube holder is closed, the sleeve of the tube holder is slid over the endotracheal tube, and its position adjusted axially along the length of the tube, and the securing clamp is closed to secure the tube holder firmly in a desired position on the endotracheal tube.

26 Claims, 2 Drawing Sheets

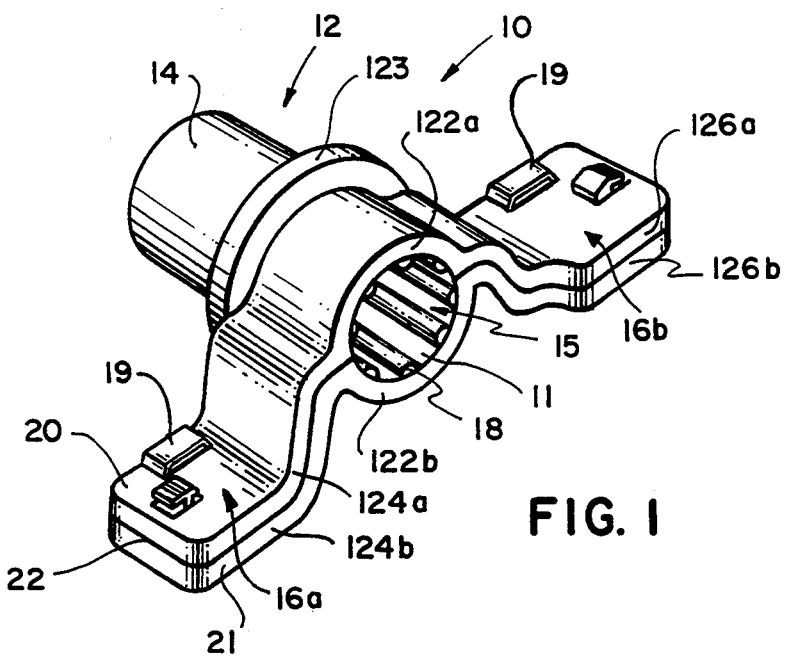
FIG. 1
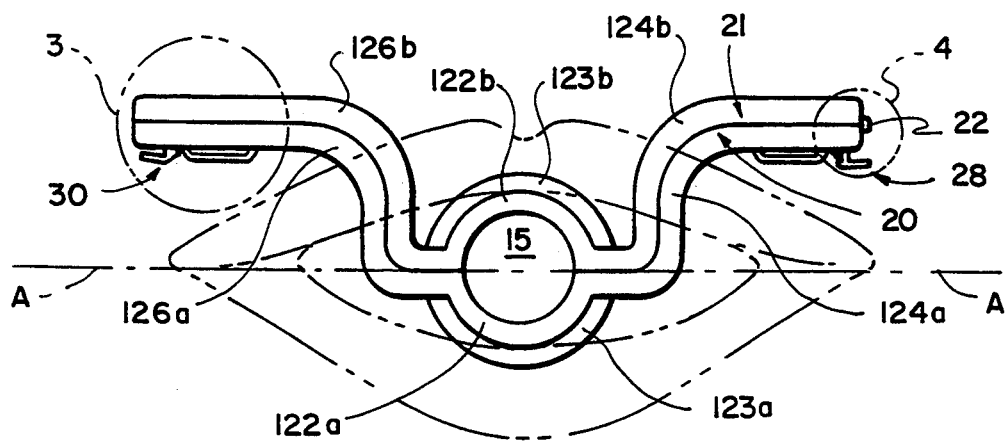
FIG. 2
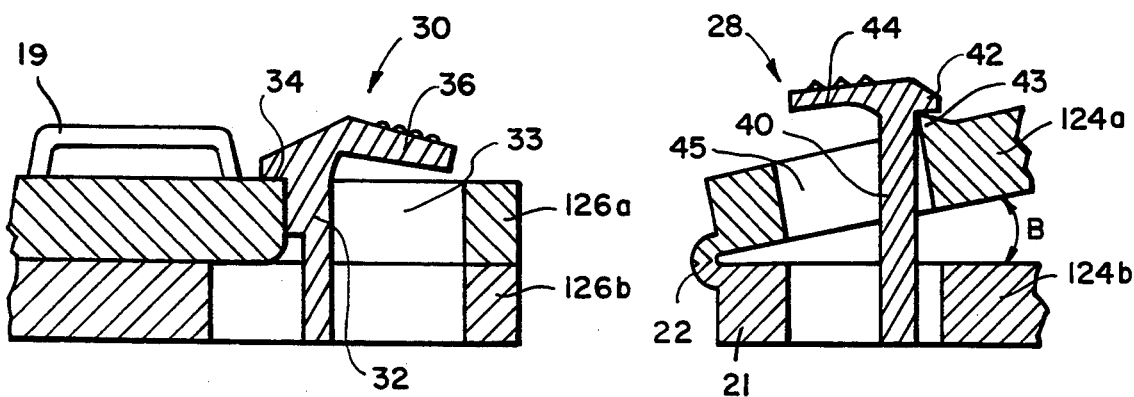
FIG. 3
FIG. 4

HINGED ENDOTRACHEAL TUBE HOLDER HAVING BOTH A SAFETY CLAMP AND A SECURING CLAMP

BACKGROUND OF THE INVENTION

The invention relates to holders for endotracheal tubes.

An endotracheal tube is generally inserted in the tracheal lumen of a patient, through the patient's mouth, to deliver air to the patient's lungs when the mouth, throat or trachea of the patient is obstructed.

It is important that the endotracheal tube be securely retained in the patient's mouth to prevent accidental removal of the tube from the tracheal lumen, which could result in asphyxiation. It is also important to minimize damage to the mucous membrane of the larynx and trachea caused by rubbing of the tube against the membrane. The tube must be retained in a manner which will secure it against shifts in the patient's position, movement of attached ventilating equipment and slippage.

Until relatively recently, endotracheal tubes were typically held in place by tape. Retaining the tube in this manner was difficult to accomplish and unreliable, as the tape would not always adhere to the patient's skin and required a relatively high degree of skill to apply quickly and securely. This method also made it impractical to adjust the orientation of the tube in the tracheal lumen after the initial insertion.

To remedy this situation, various types of endotracheal tube holders have been developed. These holders are thought to allow the tube to be more quickly and easily inserted and positioned, and may include means for preventing the patient from biting the tube. However, typically these holders do not allow the patient's mouth to be easily accessed by medical staff, e.g., for the administration of medicaments. Also, many such devices require two-handed operation and are not readily adjustable.

SUMMARY OF THE INVENTION

The present invention features an improved endotracheal tube holder which allows a patient's mouth to be readily accessed when the endotracheal tube and holder are in place, and which is easily operated and adjusted with one hand. The tube holder also provides good resistance to biting, and it is comfortable to the patient.

According to one aspect of the invention, an endotracheal tube holder for retaining an endotracheal tube in a patient's mouth comprises upper and lower portions each comprising a semi-cylindrical member and a pair of wings extending radially on opposite sides of the semi-cylindrical member. The upper portion is joined to the lower portion by a flexible hinge extending between a first wing of the upper portion and an opposed first wing of the lower portion. The wings are arranged and dimensioned so that when the hinge is in a closed position, a region of each wing of the upper portion is adjacent to a region of a corresponding opposed wing of the lower portion. The semi-cylindrical members are arranged and dimensioned so that, when the hinge is in a closed position, the semi-cylindrical members together define a sleeve, the sleeve defining a lumen dimensioned to receive the endotracheal tube. A safety clamp disposed in a region of the opposed wings adjacent the hinge is adapted to limit the extent to which the upper portion and the lower portion can pivot apart about the hinge to a predetermined maximum angle, whereby the position of the endotracheal tube in the housing can be adjusted axially and radial displacement the tube from the endotracheal tube holder is restricted. A securing clamp disposed in a region of opposed wings relatively more spaced from the hinge is adapted to be moved between a first position, in which the upper portion and the lower portion are allowed to pivot to the extent allowed by the safety clamp, to allow for axial adjustment of the endotracheal tube within the lumen, and a second position, in which the sleeve engages the tube in a manner to limit axial movement thereof of the tube relative to the endotracheal tube holder.

Preferred embodiments of this aspect of the invention may include one or more of the following additional features. The wings are arranged and dimensioned so that a major portion of each wing is removed from a horizontal plane defined by the longitudinal axis of the semi-cylindrical member and a substantially horizontal line taken radially across the semi-cylindrical member. The sleeve includes a plurality of raised structures on its inner surface. The safety clamp comprises a resilient member extending upwardly from the lower portion, through an aperture in the upper portion, the resilient member comprising a latch member adapted to engage the upper portion and a release member which, when deflected, disengages the latch member from the upper portion. Preferably, the resilient member is dimensioned to allow the upper portion and the lower portion to pivot about the hinge to define an angle of less than about 30°, and more preferably the resilient member is dimensioned to allow the upper portion and the lower portion to pivot about the hinge to define a maximum angle of from about 5° to 10°. The securing clamp comprises a resilient member which extends upwardly from the lower portion, through an aperture in the upper portion, and which includes a latch member adapted to engage the upper portion and a release member which, when deflected, disengages the latch member from the upper portion. Preferably, resilient member is dimensioned so that when the latch member engages the upper portion, the lumen defined by the upper and lower semi-cylindrical members has a predetermined diameter which is substantially equal to that of an outer surface of the endotracheal tube. A first portion of each wing, adjacent the semi-cylindrical portion, extends downwardly (or upwardly) from the horizontal plane, and a second more remote portion of each wing extends outwardly in a plane substantially parallel to the horizontal plane.

In another aspect, the invention features a method of inserting and retaining an endotracheal tube in the tracheal lumen of a patient. The method comprises the steps of: inserting the endotracheal tube through the patient's mouth into the tracheal lumen; providing an endotracheal tube holder comprising upper and lower portions each comprising a semi-cylindrical member and a pair of wings extending radially on opposite sides of the semi-cylindrical member, the upper portion being joined to the lower portion by a flexible hinge extending between a first wing of the upper portion and an opposed first wing of the lower portion, the wings being arranged and dimensioned so that when the hinge is in a closed position, a region of each upper wing is adjacent to a region of a corresponding lower wing, the semi-cylindrical members being arranged and dimensioned so that, when the hinge is in a closed position, the semi-cylindrical members together define a sleeve, the sleeve defining a lumen dimensioned to receive the endotracheal tube; a safety clamp, disposed in a region adjacent the hinge and adapted to limit the extent to which the upper portion and the lower portion can pivot apart about the hinge to a predetermined maximum angle, whereby the position of the endotracheal tube in the housing can be adjusted axially and radial displacement of the endotracheal tube from the endotracheal tube holder is restricted; and a securing clamp disposed in the region spaced further from the hinge and adapted to be moved between a first position, in which the upper portion and the lower portion are allowed to pivot apart to the extent allowed by the safety clamp, to allow for axial adjustment of the endotracheal tube within the lumen while limiting radial movement, and a second position, in which the sleeve engages the tube, thereby also limiting axial movement thereof; closing the safety clamp (without engaging the securing clamp); sliding the sleeve of the endotracheal tube holder over the endotracheal tube; adjusting the position of the endotracheal tube holder axially along the length of the endotracheal tube until the endotracheal tube holder is in a desired position; and closing the securing clamp, securing the endotracheal tube holder firmly in position on the endotracheal tube.

Preferred embodiments of this aspect of the invention may include one or more of the following additional steps. The steps of securing a neck or head strap to the wings on either side of the housing and fastening the strap about the neck or head of the patient. The step of closing the securing clamp is performed with one hand. The wings are arranged and dimensioned so that a major portion of each wing is removed from a horizontal plane defined by the longitudinal axis of the semi-cylindrical member and a substantially horizontal line taken radially across the semi-cylindrical member. The sleeve includes a plurality of raised structures on its inner surface. The safety clamp comprises a resilient member which extends upwardly from the lower portion, through an aperture in the upper portion, and which includes a latch member adapted to engage the upper portion and a release member which, when deflected, disengages the latch member from the upper portion. The resilient member is dimensioned to allow the upper portion and the lower portion to pivot about the hinge to define an angle of less than about 30°, preferably, the resilient member is dimensioned to allow the upper portion and the lower portion to pivot about the hinge to define a maximum angle of from about 5° to 10°. The securing clamp comprises a resilient member which extends upwardly from the lower portion, through an aperture in the upper portion, and which includes a latch member adapted to engage the upper portion and a release member which, when deflected, disengages the latch member from the upper portion. The resilient member is dimensioned so that when the latch member engages the upper portion the lumen defined by the upper and lower semi-cylindrical members has a predetermined diameter which is substantially equal to that of an outer surface of the endotracheal tube. A first portion of each wing, adjacent the semi-cylindrical portion, extends downward from the horizontal plane, and a second more remote portion of each wing extends outwardly in a plane substantially parallel to the horizontal plane.

Other features and advantages of the invention will be apparent from the following description of presently preferred embodiments, and from the claims.

BRIEF DESCRIPTION OF THE DRAWINGS

FIG. 1 is perspective view of an endotracheal tube holder according to one embodiment of the invention.

FIG. 2 is a front view of the tube holder of FIG. 1.

FIG. 3 is an enlarged cross-sectional view of Detail 3 in FIG. 2.

FIG. 4 is an enlarged cross-sectional view of Detail 4 in FIG. 2.

DESCRIPTION OF THE PREFERRED EMBODIMENTS

Figure 3A:
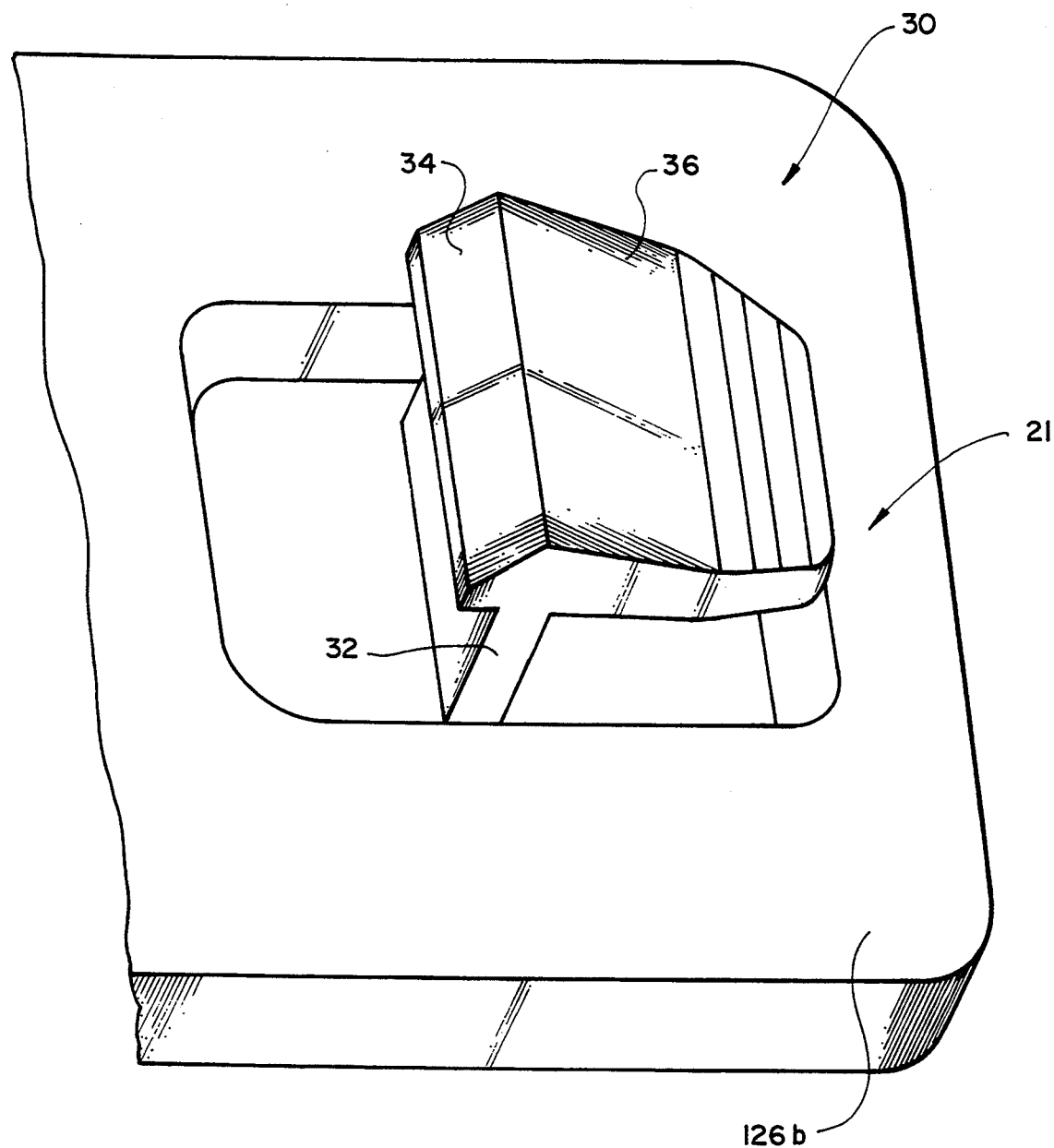
FIG. 3a is a highly enlarged perspective view of the clamp shown in FIG. 3.

Referring to FIGS. 1 and 2, a preferred endotracheal tube holder 10 of the invention includes an integral housing 12 having a "clamshell" type structure, i.e., housing 12 comprises two halves, upper half 20 and lower half 21, which are joined by a flexible hinge 22. Each half comprises a semi-cylindrical portion 122a, 122b, and a pair of wings 124a, 124b, and 126a, 126b.

When hinge 22 is in a closed position, as shown in FIG. 1, semi-cylindrical portions 122a, 122b form an annular sleeve 14. Sleeve 14 defines a lumen 15, dimensioned to receive an endotracheal tube (not shown). Sleeve 14 is preferably formed of a rigid, resilient material, e.g., polypropylene, which has sufficient rigidity to act as a bite guard for the endotracheal tube, preventing the patient from damaging or closing the tube by biting down on it, and sufficient resiliency to provide cushioning for patient comfort. Preferably, sleeve 14 has a plurality of longitudinal ribs 18 on its inner surface 11, to provide a more positive grip of the sleeve about the endotracheal tube extending therethrough. A flange 123, having portions 123a, 123b, extends radially from the outer surface of the sleeve in a manner to aid in longitudinal positioning of the sleeve by engaging gently against a patient's upper and lower front teeth, as described in more detail below.

Each pair of adjacent wings, i.e., pairs 124a, 124b and pairs 126a, 126b, forms a wing structure 16a, 16b when hinge 22 is in a closed position, as shown in FIGS. 1 and 2. The two wing structures curve upwardly, out of a plane defined by the axis of the tube and sleeve 14 and a horizontal line A across the patient's mouth, to allow easy access to the patient's mouth on either side of the housing in a manner to facilitate more thorough and efficient mouth care. Two neck/head strap holders 19 are mounted on the housing, one on each wing, to receive a strap (not shown) which is fastened behind the patient's neck or head.

The diameter of lumen 15 defined by sleeve 14 is determined by the spacing between the semi-cylindrical members. To adjust this spacing, and to hold the upper and lower halves relatively close together, so that the holder can be manipulated with one hand, the housing is provided with a pair of clamps. In the preferred embodiment shown, the housing includes a securing clamp 30 on wing 16b and a safety clamp 28 on wing 16a.

Safety clamp 28, which is closest to hinge 22, is provided to act as a stop, limiting the amount of separation between the two halves, preferably to an extent so that, when the hinge is open to the fullest extent allowed by the safety clamp, a lumen is still defined by the semi-cylindrical portions at least to an extent to prevent radial displacement of the tube from the lumen. However, the safety clamp allows the diameter of the lumen to be increased sufficiently to allow axial adjustment of the endotracheal tube, also without allowing the two halves to become so separated that it is difficult to close them with one hand.

Referring to FIG. 4, safety clamp 28, shown in detail, comprises a resilient member 40 which extends upwardly from wing 124b of the lower half 21 of the housing, through aperture 45 in opposed wing 124a. Resilient member 40 includes a latch member 42 and a release member 44. Wing 124a defines a shoulder 43, positioned for engagement by latch member 42. Resilient member 40 is dimensioned so that, when latch member 42 and shoulder 43 are engaged, as shown in FIG. 4, the two halves of the housing can be separated (pivoted about hinge 22) to define a maximum angle B therebetween. Preferably, angle B is less than about 30°, more preferably angle B is about 5° to 10°. If it is desired to open the two halves beyond the extent allowed by the safety latch, latch member 42 may be released from shoulder 43 by depressing release member 44.

Securing clamp 30, when engaged, clamps the housing around the tube, thereby securely holding the tube against both axial and radial displacement, and, when disengaged, allows the housing to open to the extent allowed by safety clamp 28.

Referring to FIGS. 3 and 3a, securing clamp 30, shown in detail, comprises resilient member 32, which extends upwardly from wing 126b of lower half 21, through aperture 33 in wing 126a. Resilient member 32 includes latch member 34 and release member 36. Securing clamp 30 functions in the same manner as does safety clamp 28, i.e., the latch member engages the upper wing until it is released therefrom by depressing the release member. (Apertures in the wings 124b, 126b (FIGS. 3a and 4, respectively) facilitate the manufacturing process.)

In use, an endotracheal tube is first inserted through the patient's mouth into the tracheal lumen. Then, with the safety clamp closed and the securing clamp open, the sleeve of the holder is slid over the endotracheal tube and the position of the holder is adjusted axially along the tube until the holder is in a desired position, preferably with the flange portions engaged gently against the patient's teeth. A neck/head strap, attached to the wings on either side of the housing, is then typically fastened about the neck or head of the patient. When a desired position is achieved, the securing clamp is then closed, typically with one hand, securing the tube firmly in position within the holder. If further adjustment of the holder later becomes necessary, this can easily be accomplished by unfastening the securing clamp, sliding the tube axially within the lumen of the holder, and refastening the securing clamp.

Other embodiments are within the claims. For example, the ribs 18 on sleeve 14 may, in the alternative, be axial or spiral. Where desired for increased security against accidental or inadvertent release, e.g. due to movement or actions by a patient, a second securing clamp may be provided, preferably at right angle to the first securing clamp, thus to require use of two hands for release of the device.

What is claimed is:

1. An endotracheal tube holder for retaining an endotracheal tube in a patient's mouth comprising:
   an upper portion and a lower portion,
   said upper portion and said lower portion each comprising a semi-cylindrical member and a pair of wings extending radially on opposite sides of said semi-cylindrical member, said upper portion being Joined to said lower portion by a flexible hinge extending between a first said wing of said upper portion and an opposed first said wing of said lower portion,
   said wings being arranged and dimensioned so that when said hinge is in a closed position, a region of each wing of said upper portion is adjacent to a region of a corresponding opposed wing of said lower portion, and
   said semi-cylindrical members being arranged and dimensioned so that, when said hinge is in a closed position, the semi-cylindrical members together define a lumen dimensioned to receive the endotracheal tube;
   a safety clamp, disposed in a region of the opposed wings adjacent said hinge and including means for limiting, by interference engagement, the extent to which said upper portion and said lower portion can pivot apart about said hinge to a predetermined maximum angle, said predetermined angle being sufficiently large to allow the position of the endotracheal tube in the housing to be adjusted axially, and sufficiently small so that said tube cannot be radially displaced from the endotracheal tube holder when the safety clamp is engaged; and
   a securing clamp disposed in a region of the opposed wings relatively more spaced from said hinge and resiliently movable between a first position, in which said upper portion and said lower portion are allowed to pivot to the extent allowed by said safety clamp, to allow for axial adjustment of the endotracheal tube within said lumen, and a second position, in which the semi-cylindrical members engage the tube in a manner to limit axial movement of the tube relative to said endotracheal tube holder.

2. An endotracheal tube holder of claim 1 wherein said wings are arranged and dimensioned so that a major portion of each wing is removed from a horizontal plane defined by the longitudinal axis of the semi-cylindrical member and a substantially horizontal line taken radially across the semi-cylindrical member.

3. An endotracheal tube holder of claim 2 wherein a first portion of each said wing, adjacent said semi-cylindrical portion, extends downwardly from said horizontal plane, and a second, more remote portion of each said wing extends outwardly in a plane substantially parallel to said horizontal plane.

4. An endotracheal tube holder of claim 1 wherein said semi-cylindrical members include a plurality of raised structures on their inner surfaces.

5. An endotracheal tube holder of claim 1 wherein said safety clamp comprises a resilient member extending upwardly from said lower portion, through an aperture in said upper portion, said resilient member comprising a latch member adapted to engage said upper portion, and a release member which, when deflected, disengages said latch member from said upper portion.

6. An endotracheal tube holder of claim 5 wherein said resilient member is dimensioned to allow said upper portion and said lower portion to pivot about said hinge to define an angle of less than about 30°.

7. An endotracheal tube holder of claim 6 wherein said resilient member is dimensioned to allow said upper portion and said lower portion to pivot about said hinge to define a maximum angle of from about 5° to 10°.

8. An endotracheal tube holder of claim 1 wherein said securing clamp comprises a resilient member which extends upwardly from said lower portion, through an aperture in said upper portion, and which includes a latch member adapted to engage said upper portion and a release member which, when deflected, disengages said latch member from said upper portion.

9. An endotracheal tube holder of claim 8 wherein said resilient member is dimensioned so that when said latch member engages said upper portion, the lumen defined by the upper and lower semi-cylindrical members has a predetermined diameter which is substantially equal to that of an outer surface of the endotracheal tube.

10. A method of inserting and retaining an endotracheal tube in the tracheal lumen of a patient comprising the steps of:
  inserting the endotracheal tube through the patient's mouth into the tracheal lumen;
  providing an endotracheal tube holder comprising: an upper portion and a lower portion, said upper portion and said lower portion each comprising a semi-cylindrical member and a pair of wings extending radially on opposite sides of said semi-cylindrical member, said upper portion being joined to said lower portion by a flexible hinge extending between a first said wing of said upper portion and an opposed first said wing of said lower portion, said wings being arranged and dimensioned so that when said hinge is in a closed position, a region of each upper wing is adjacent to a region of a corresponding lower wing, said semi-cylindrical members being arranged and dimensioned so that, when said hinge is in a closed position, the semi-cylindrical members together define a lumen dimensioned to receive the endotracheal tube; a safety clamp disposed in a region adjacent said hinge and adapted, by interference engagement, to limit the extent to which said upper portion and said lower portion can pivot apart about said hinge to a predetermined maximum angle; and a securing clamp disposed in a region spaced further from said hinge;
  dimensioning and positioning the safety clamp so that the predetermined maximum angle is sufficiently large to allow the position of the endotracheal tube in the housing to be adjusted axially, and sufficiently small so that the tube cannot be radially displaced from the endotracheal tube holder when the safety clamp is engaged;
  dimensioning and positioning the securing clamp so that it can be moved between a first position, in which the securing clamp is disengaged and the upper portion and the lower portion are allowed to pivot apart to the extent allowed by the safety clamp and a second position, in which the sleeve engages the tube, to limit axial movement of the tube relative to the lumen;
  sliding the endotracheal tube holder over the endotracheal tube so that the tube is received in the lumen;
  closing the safety clamp;
  with the securing clamp disengaged, adjusting the position of the endotracheal tube holder axially along the length of the endotracheal tube until the endotracheal tube holder is in a desired position; and
  closing the securing clamp, thereby securing the endotracheal tube holder firmly in position on the endotracheal tube.

11. A method of claim 10, further comprising the steps of securing a neck/head strap to the wings on either side of the housing and fastening the strap about the neck or head of the patient.

12. A method of claim 10, wherein said step of closing the securing clamp is performed with one hand.

13. A method of claim 10 further comprising the step of dimensioning and arranging the wings so that a major portion of each wing is removed from a horizontal plane defined by the longitudinal axis of the semi-cylindrical member and a substantially horizontal line taken radially across the semi-cylindrical member allowing the further steps of, after the securing clamp is engaged, accessing the patient's mouth on either side of the housing and performing mouth care.

14. A method of claim 10 wherein the safety clamp comprises a resilient safety clamp member which extends upwardly from the lower portion, and a safety clamp latch member extending from the resilient safety clamp member and positioned for interference engagement with a region of the upper portion, and said step of closing the safety clamp includes inserting the resilient safety clamp member through an aperture in the upper portion in manner to cause inference engagement of the safety clamp latch member with a region of the upper portion adjacent the aperture.

15. A method of claim 14 further comprising the step of dimensioning the resilient safety clamp member to allow the upper potion and the lower portion to pivot about the hinge to define an angle of less than about 30° when the safety clamp is closed and in interference engagement.

16. A method of claim 15 further comprising the step of, after closing the safety clamp, pivoting the upper portion and the lower portion about the hinge to define a maximum angle of from about 5° to 10°.

17. A method of claim 14 wherein the safety clamp further comprises a safety clamp release member, adjacent the safety clamp latch member, shaped and positioned to when deflected, disengage the safety clamp latch member from the upper portion, and said method further includes, after the step of closing the securing clamp, the sequential steps of releasing the securing clamp, removing the tube holder form the endotracheal tube, and releasing the safety clamp by deflecting the release member to disengage the safety clamp latch member from the upper portion.

18. A method of claim 10 wherein the securing clamp comprises a resilient securing member which extends upwardly from the lower portion, and a securing latch member extending from the resilient securing member, and said step of closing the securing clamp includes inserting the resilient securing member through an aperture in the upper portion to place the securing latch member in interference engagement with a region of the upper portion adjacent the aperture.

19. A method of claim 18 further comprising the step of dimensioning the resilient securing member so that when the securing latch member engages the region of the upper portion, the lumen defined by the upper and lower semi-cylindrical members has a predetermined diameter which is substantially equal to that of the outer surface of the endotracheal tubes.

20. A method of claim 18 wherein the securing clamp further comprises a securing clamp release member, adjacent the securing latch member, shaped and positioned to, when deflected, disengage the securing latch member from the upper portion, and said method further includes the step of, after the step of closing the securing clamp, releasing the securing clamp by deflecting the securing clamp release member to disengage the securing latch member from the upper portion.

21. An endotracheal tube holder for retaining an endotracheal tube in a patient's mouth comprising:

an upper portion and a lower portion,
said upper portion and said lower portion each comprising a semi-cylindrical member and a pair of wings extending radially on opposite sides of said semi-cylindrical member, said upper portion being joined to said lower portion by a flexible hinge extending between a first said wing of said upper portion and an opposed first said wing of said lower portion,
said wings being arranged and dimensioned so that when said hinge is in a closed position, a region of each wing of said upper portion is adjacent to a region of a corresponding opposed wing of said lower portion, and
said semi-cylindrical members being arranged and dimensioned so that, when said hinge is in a closed position, the semi-cylindrical members together define a lumen dimensioned to receive the endotracheal tube;
a safety clamp, disposed in a region of the opposed wings and including means for limiting, by interference engagement, the extent to which said upper portion and said lower portion can pivot apart about said hinge to a predetermined maximum angle, said predetermined maximum angle being sufficiently large to allow the position of the endotracheal tube in the housing to be adjusted axially, and sufficiently small so that said tube cannot be radially displaced from the endotracheal tube holder when said safety clamp is engaged; and
a securing clamp disposed in a region of the opposed wings and adapted to be moved between a first position, in which said upper portion and said lower portion are allowed to pivot to the extent allowed by said safety clamp, to allow for axial adjustment of the endotracheal tube within said lumen, and a second position, in which the semi-cylindrical members engage the tube in a manner to limit axial movement of the tube relative to said endotracheal tube holder.

22. An endotracheal tube holder for retaining an endotracheal tube in a patient's mouth comprising:

an upper portion and a lower portion,
said upper portion and said lower portion each comprising a semi-cylindrical member and a pair of wings extending radially on opposite sides of said semi-cylindrical member, said upper portion being joined to said lower portion by a flexible hinge extending between a first said wing of said upper portion and an opposed first said wing of said lower portion,
said wings being arranged and dimensioned so that when said hinge is in a closed position, a region of each wing of said upper portion is adjacent to a region of a corresponding opposed wing of said lower portion, and
said semi-cylindrical members being arranged and dimensioned so that, when said hinge is in a closed position, the semi-cylindrical members together define a lumen dimensioned to receive the endotracheal tube;
a safety clamp, disposed in a region of the opposed wings adjacent said hinge and including means for limiting, by interference engagement, the extent to which said upper portion and said lower portion can pivot apart about said hinge to a predetermined maximum angle of from about 5° to 10° when the safety clamp is engaged; and
a securing clamp disposed in a region of the opposed wings relatively more spaced from said hinge and resiliently movable between a first position, in which said upper portion and said lower portion are allowed to pivot to the extent allowed by said safety clamp, to allow for axial adjustment of the endotracheal tube within said lumen, and a second position, in which the semi-cylindrical members engage the tube in a manner to limit axial movement of the tube relative to said endotracheal tube holder.

23. An endotracheal tube holder of claim 22, 21 or 20, wherein said wings are arranged and dimensioned so that a major portion of each wing is removed from a horizontal plane defined by the longitudinal axis of the semi-cylindrical member and a substantially horizontal line taken radially across the semi-cylindrical member.

24. An endotracheal tube holder of claim 23 wherein a first portion of each said wing, adjacent said semi-cylindrical portion, extends downwardly from said horizontal plane, and a second, more remote portion of each said wing extends outwardly in a plane substantially parallel to said horizontal plane.

25. An endotracheal tube holder for retaining an endotracheal tube in a patient's mouth comprising:

an upper portion and a lower portion,
said upper portion and said lower portion each comprising a semi-cylindrical member and a pair of wings extending radially on opposite sides of said semi-cylindrical member, said upper portion being joined to said lower portion by a flexible hinge extending between a first said wing of said upper portion and an opposed first said wing of said lower portion,
said upper and lower portions being movable about said hinge between a first, closed position and a second open position in which said upper and lower members define an angle of greater than about 30°;
said wings being arranged and dimensioned so that when said hinge is in a closed position, a region of each wing of said upper portion is adjacent to a region of a corresponding opposed wing of said lower portion, and
said semi-cylindrical members being arranged and dimensioned so that, when said hinge is in a closed position, the semi-cylindrical members together define a lumen dimensioned to receive the endotracheal tube;
a safety clamp, disposed in a region of the opposed wings adjacent said hinge and movable between a first position in which said safety clamp is disengaged, and a second position in which said safety clamp is engaged, said safety clamp including means for limiting, by interference engagement, the extent to which said upper portion and said lower portion can pivot apart about said hinge to a predetermined maximum angle of less than about 30° when the safety clamp is engaged; and a securing clamp disposed in a region of the opposed wings relatively more spaced from said hinge and resiliently movable between a first position, in which said upper portion and said lower portion are allowed to pivot to the extent allowed by said safety clamp, to allow for axial adjustment of the endotracheal tube within said lumen, and a second position, in which the semi-cylindrical members engage the tube in a manner to limit axial movement of the tube relative to said endotracheal tube holder.

26. An endotracheal tube holder for retaining an endotracheal tube in a patient's mouth comprising:

an upper portion and a lower portion, said upper portion and said lower portion each comprising a semi-cylindrical member and a pair of wings extending radially on opposite sides of said semi-cylindrical member, said upper portion being joined to said lower portion by a flexible hinge extending between a first said wing of said upper portion and an opposed first said wing of said lower portion, said wings being arranged and dimensioned so that when said hinge is in a closed position, a region of each wing of said upper portion is adjacent to a region of a corresponding opposed wing of said lower portion, and said semi-cylindrical members being arranged and dimensioned so that, when said hinge is in a closed position, the semi-cylindrical members together define a lumen dimensioned to receive the endotracheal tube;

a safety clamp, disposed in a region of the opposed wings adjacent said hinge and comprising a resilient member extending upwardly from said one of said upper and lower portions, through an aperture in the opposite lower or upper portion, said resilient member comprising a latch member adapted to engage said opposite portion, and a release member which, when deflected, disengages said latch member from said opposite portion; and a securing clamp disposed in a region of the opposed wings relatively more spaced from said hinge and resiliently movable between a first position, in which said upper portion and said lower portion are allowed to pivot to the extent allowed by said safety clamp, to allow for axial adjustment of the endotracheal tube within said lumen, and a second position, in which the semi-cylindrical members engage the tube in a manner to limit axial movement of the tube relative to said endotracheal tube holder.

* * * * *